(12) United States Patent
Mitelberg et al.

(10) Patent No.: US 11,090,041 B2
(45) Date of Patent: Aug. 17, 2021

(54) DEVICE AND METHOD FOR SECURING ENDOSCOPE RELATIVE TO SUTURING SYSTEM

(71) Applicant: Apollo Endosurgery US, Inc., Austin, TX (US)

(72) Inventors: Vladimir Mitelberg, Austin, TX (US); John Mims, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 805 days.

(21) Appl. No.: 15/868,302

(22) Filed: Jan. 11, 2018

(65) Prior Publication Data

US 2019/0209160 A1 Jul. 11, 2019

(51) Int. Cl.
| | |
|---|---|
| *A61B 1/00* | (2006.01) |
| *A61B 17/04* | (2006.01) |
| *A61B 1/018* | (2006.01) |
| *A61B 17/062* | (2006.01) |
| *A61B 17/00* | (2006.01) |

(52) U.S. Cl.
CPC ...... *A61B 17/0469* (2013.01); *A61B 1/00087* (2013.01); *A61B 1/00089* (2013.01); *A61B 1/00101* (2013.01); *A61B 1/00137* (2013.01); *A61B 1/018* (2013.01); *A61B 1/0008* (2013.01); *A61B 17/0485* (2013.01); *A61B 17/0487* (2013.01); *A61B 17/0625* (2013.01); *A61B 2017/0034* (2013.01); *A61B 2017/00296* (2013.01)

(58) Field of Classification Search
CPC ...... A61B 2017/00296; A61B 1/00087; A61B 1/00089; A61B 1/0014; A61B 1/012; A61B 1/018; A61B 17/062; A61B 17/0625; A61B 1/0008; A61B 1/00098; A61B 1/00101; A61B 1/0011; A61B 1/00137
USPC .................. 600/104, 106–107, 127, 129
See application file for complete search history.

(56) References Cited

U.S. PATENT DOCUMENTS

| | | | |
|---|---|---|---|
| 8,684,912 B2 * | 4/2014 | Deviere | A61B 1/0014 600/114 |
| 8,876,701 B2 * | 11/2014 | Surti | A61B 17/0469 600/127 |

* cited by examiner

*Primary Examiner* — Ryan N Henderson
*Assistant Examiner* — Pamela F Wu
(74) *Attorney, Agent, or Firm* — Brian Szymczak

(57) ABSTRACT

A distal cap apparatus for use with an endoscope, having a proximal end and a distal end and a longitudinal axis extending therebetween, includes a mount configured for mounting to the distal end of the endoscope, and a strap connected to the mount and configured for banding about the distal end of the endoscope when the distal end of the endoscope is received in the mount. The mount defines a strap slot configured to receive an end of the strap to configure the strap in the banded configuration. The strap may be elastic. A tool is provided to facilitate properly seating of the strap within the mount of the cap assembly. The tool includes a window and a swing arm rotatable within the window to cause a portion of the arm to contact a free end of the strap to force the strap into a fully seated position.

27 Claims, 14 Drawing Sheets

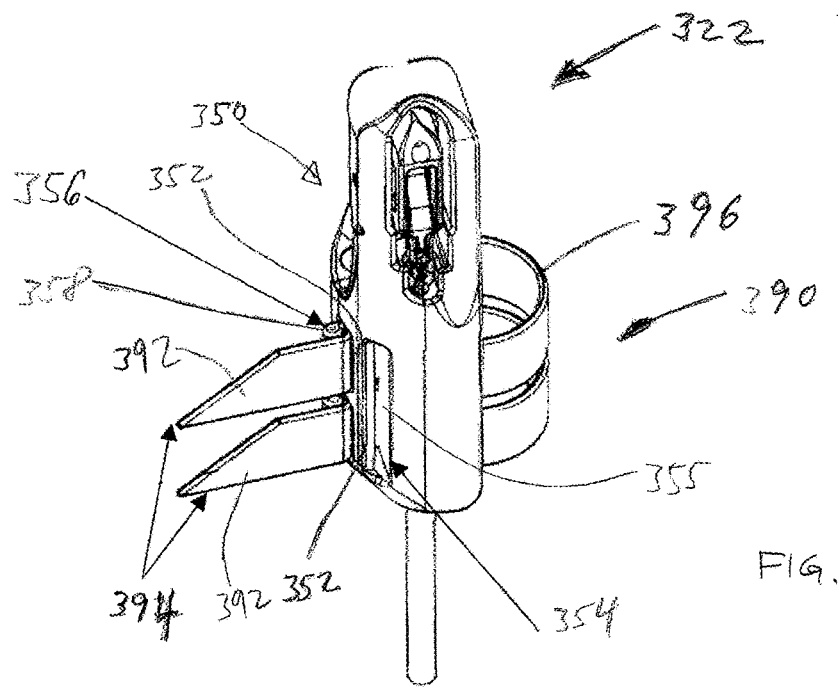
FIG. 13
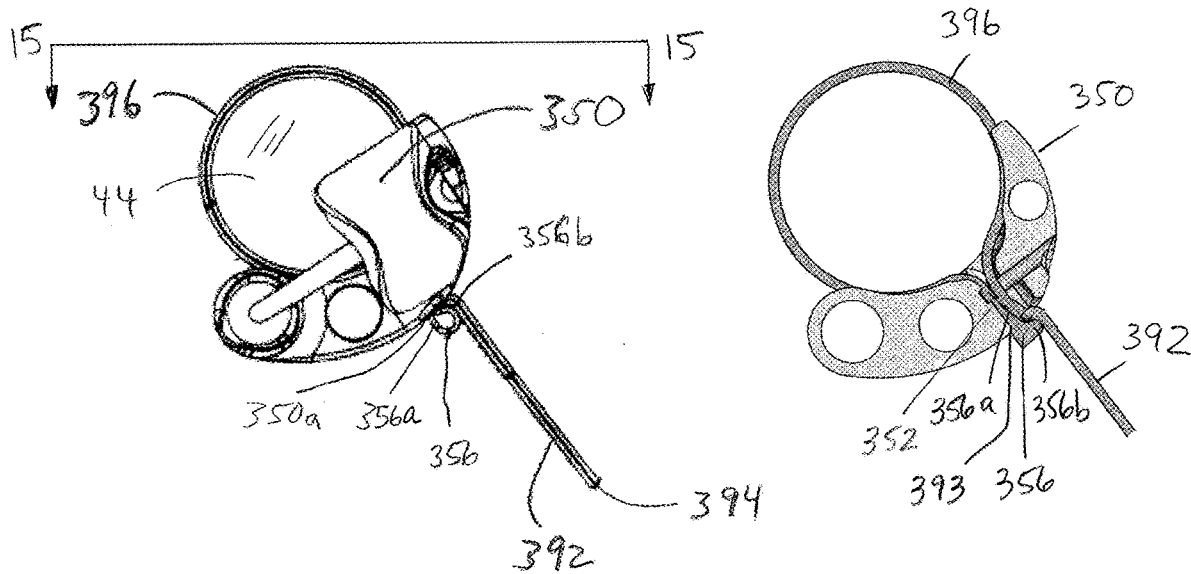
FIG. 14
FIG. 15

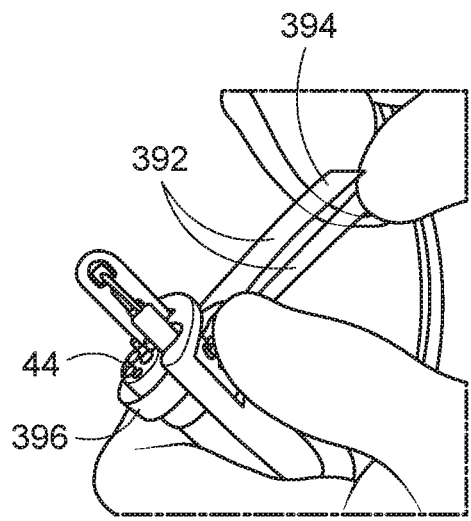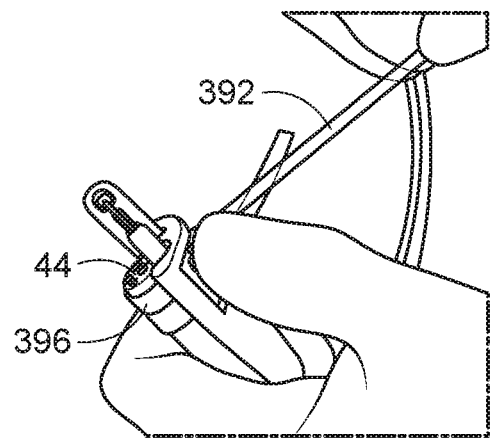
FIG. 21A   FIG. 21B
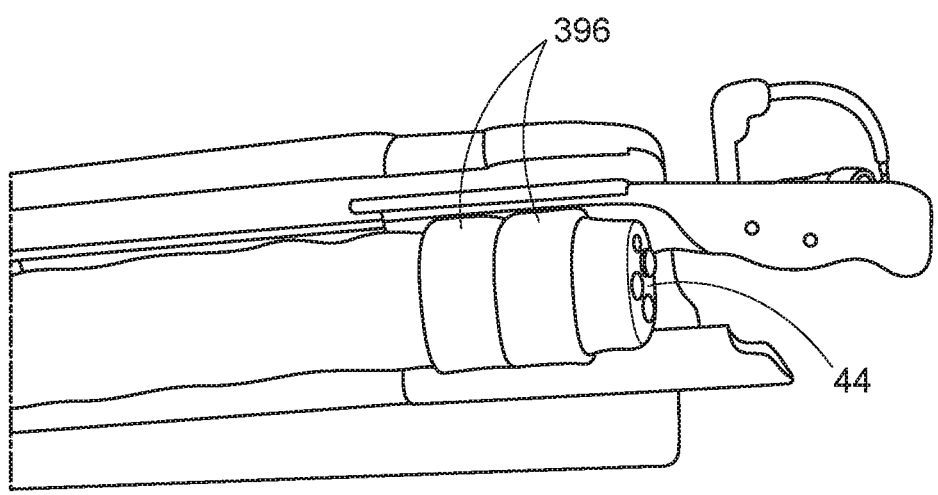
FIG. 21C

DEVICE AND METHOD FOR SECURING ENDOSCOPE RELATIVE TO SUTURING SYSTEM

CROSS-REFERENCE TO RELATED APPLICATIONS

This application is related to U.S. Ser. No. 15/468,962, filed Mar. 24, 2017, which is a continuation-in-part of U.S. Ser. No. 15/233,737, filed Aug. 10, 2016, both of which are hereby incorporated by reference herein in their entireties.

This application is also related to U.S. Pat. Nos. 8,287,556, 8,679,136, and 9,198,562, which are hereby incorporated by reference herein in their entireties.

BACKGROUND

1. Field

The present invention relates to endoscopic instruments. More particularly, the present invention relates to installation tools for use with a treatment device that can be inserted into a body through a natural orifice with an endoscope or other steerable guide member. The present invention may be used to perform suturing on the tissue of a mammal, whether human or not, and whether or not alive, but is not limited thereto.

2. State of the Art

U.S. Pat. No. 7,344,545 to Takemoto discloses an endoscopic suturing system having many embodiments to perform a surgical operation. This suturing system generally comprises an assembly having first and second arms which are actuatable by a push rod to rotatably approach each other while one arm grasps tissue and the second arm drives a curved needle through the tissue. The system also includes a needle recovery member requiring a rigid alignment with the curved needle arm. While this system affords the ability to grasp thick tissue, the tissue grasping arm and the arrangement of the needle recovery member provides bulk to the system making it difficult to use in endoscopic procedures.

Co-owned U.S. Pat. No. 8,287,556 to Gilkey et al. describes a system that addresses various limitations of the system by Takemoto. Gilkey describes an endoscopic treatment device having a structure enabling a small profile for delivery while providing an end effector with both a wide opening and closing angle that produces the large needle force for piercing tissue to perform a surgical operation such as tissue approximation and suturing within the body.

The Gilkey system comprises a transmission assembly coupled to a proximal handle assembly for operation outside of the body and a distal cap assembly where the cap assembly is adapted to engage the distal end of an endoscope. The transmission assembly is connected to a link mechanism and is actuated to cause a needle assembly having a needle holder arm and needle coupled to the cap assembly to move in a direction to puncture tissue and a direction to be removed from tissue. The endoscope to which the cap assembly is coupled has first and second instrument channels to receive cooperative devices therethrough. The first device is positioned within the first instrument channel of the endoscope and has a distal end adapted to receive and grasp the needle and a proximal end coupled to a handle assembly. The second device is positioned within the second instrument channel of the endoscope to engage tissue, and draw the tissue back into the path of the needle so that the tissue can be pierced by the needle as the needle is moved from an open to a closed position.

While the Gilkey system works very well, it presently requires association with an endoscope having two instrument channels. This may limit use of the system to larger endoscopes with such features. However, smaller endoscopes are gaining favor. Such smaller endoscopes, with their smaller profile, can be more easily advanced through a natural orifice. However, the reduced profile of the smaller endoscopes cannot accommodate the two instrument channels required for the Gilkey suturing system.

Co-owned U.S. Ser. Nos. 15/468,962 and 15/233,737 to Mitelberg, previously incorporated herein, disclose a different suturing system designed to accommodate small diameter endoscopes. The system, for use with an endoscope, includes a suturing device defining first and second throughbores external of the endoscope, a needle assembly movable through tissue by the suturing device, and first and second devices used in association with the suturing device. The endoscope can be a small profile endoscope, generally 5-10 mm in diameter, and can have one or more instrument channels, and optionally no instrument channel. As such, the number of instrument channels is not critical to operation of the system. The suturing device includes a distal cap assembly adapted to be mounted at the distal end of the endoscope, and transmission assembly extending between the cap assembly and a proximal handle adapted to apply a force to the transmission assembly and operate the cap assembly remotely from the distal cap assembly. The cap assembly includes a mount, a support bracket extending distally from the mount, and a needle arm rotatably mounted on the bracket. A bell crank is also rotatably mounted on the support bracket and engages the needle arm. The distal end of the transmission assembly is attached to the bell crank, such that when the transmission assembly is operated by the handle, movement of the bell crank causes rotation of the needle arm between the open and closed positions. The mount is structured such that when the cap assembly is coupled to the endoscope, the first and second throughbores are positioned radially outside the profile of the endoscope. In an embodiment, a distal cap includes at least one strap connected to the mount and configured for banding about the distal end of the endoscope when the distal end of the endoscope is received in the mount. The mount defines at least one strap slot configured to receive an end of each strap to position the strap in the banded configuration about the endoscope. The strap slot may be configured to frictionally engaged the strap positioned relative to the strap slot when the strap is pulled through the strap slot.

However, if the strap is not fully seated within the mount of the cap assembly, the attachment and interface between the endoscope and cap assembly would not be as designed and intended. Then, it is possible that environmental forces and conditions could result in inadvertent release of strap and loosening of the cap assembly relative to the endoscope.

SUMMARY

A tool is provided to facilitate seating of the strap within the mount of the cap assembly. The tool includes a body adapted to partially surround the mount. The body includes an inner surface for contacting the mount, and an outer surface forming a hand-hold. The body includes a stop for aligning the mount relative to the body, a retainer that engages the mount to retain the mount relative to the body, and a release for releasing the retainer. A window is defined in the body, and a swing arm is hingedly coupled to the body and rotatable relative to and within the window. The swing arm includes a pusher adapted to move through the window and into a portion of the strap slot. When the inner surface and retainer of the tool engage the mount, the pusher of the swing arm may be rotated within the window of the mount to cause the pusher to contact the free end of the straps to force the strap into a fully seated position.

BRIEF DESCRIPTION OF THE DRAWINGS

FIG. 13 is a perspective distal end view of another embodiment of a cap assembly that is configured for attachment at the distal end of an endoscope of the endoscope suturing system.

FIG. 14 is a top plan view of the cap assembly of FIG. 13.

FIG. 15 is a section view across line 15-15 in FIG. 14.

FIGS. 20A through 25 show a method of assembly of a cap assembly of FIG. 13 to an endoscope using the tool of FIG. 16.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use.

Figure 1:
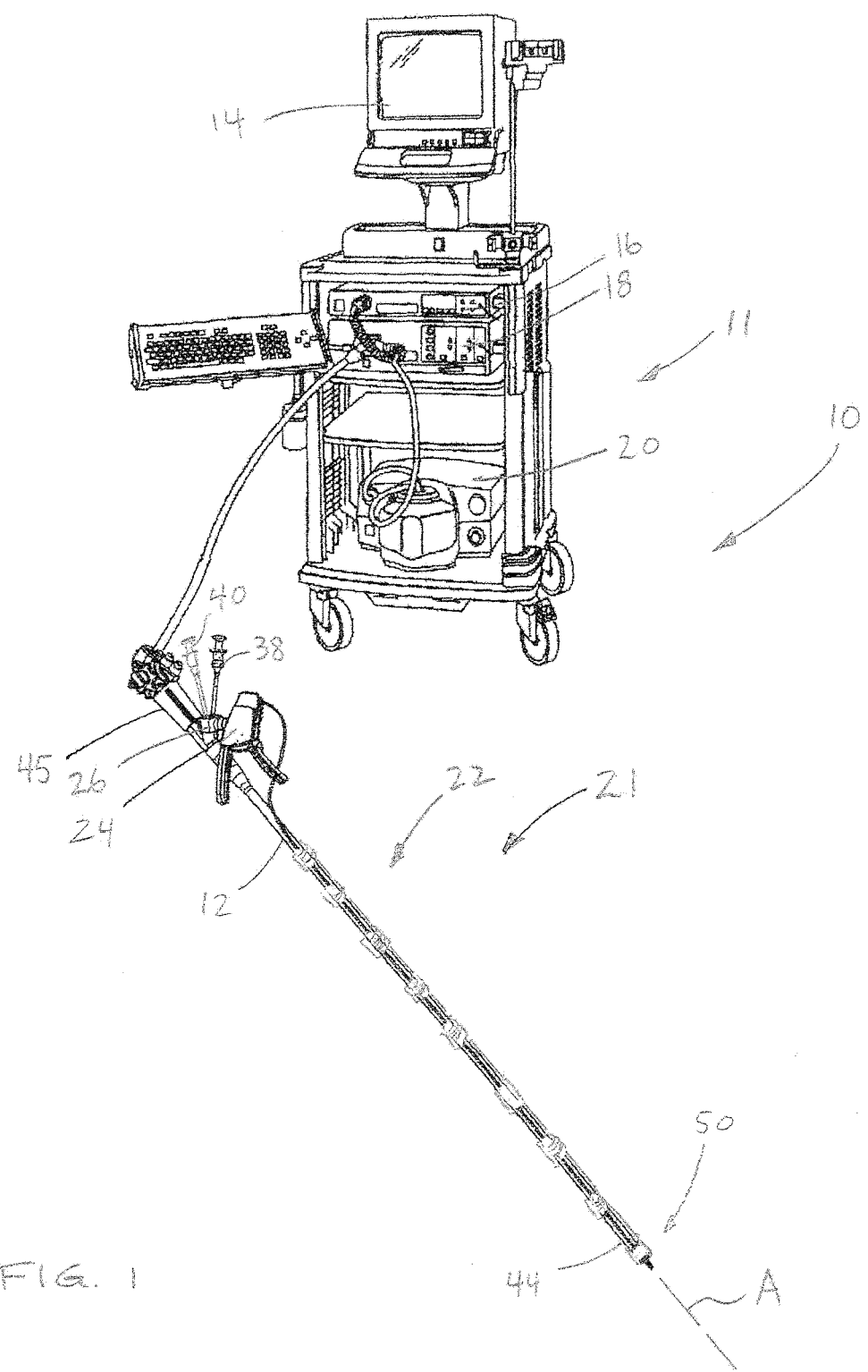
FIG. 1 is a perspective view of an endoscopic suturing system according an embodiment of the invention.
Figure 4:
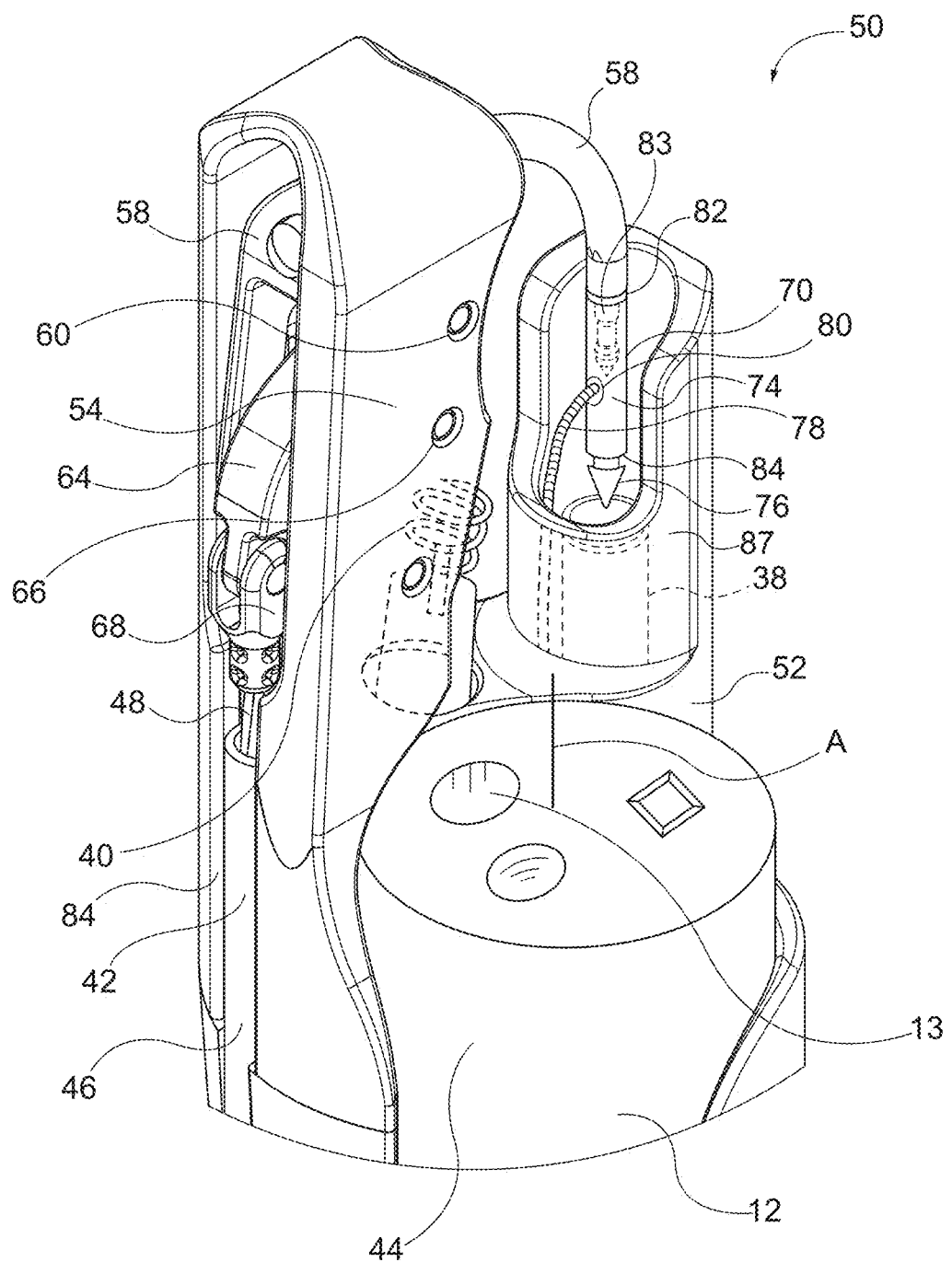
FIG. 4 is a perspective distal end view of an embodiment of a cap assembly attached at the distal end of an endoscope of the endoscope suturing system.

Referring to FIG. 1, an endoscopic treatment system 10 includes an endoscope system 11 and an endoscopic suturing system 22. The endoscope system 11 includes an endoscope 12, a video display unit 14, an image processing device 16, a light source 18, and a suction device 20. In accord with an embodiment, the endoscope 12 has a small profile, generally 5-10 mm in diameter. However, the size of the endoscope is not critical, and elements described herein can be adapted for endoscopes of other sizes. In the embodiment shown, the endoscope 12 has a single instrument channel 13 (FIG. 4). However, the endoscope may have more than one instrument channel or no instrument channel all, as operation of the system does not necessarily require use of the instrument channel through the endoscope. The endoscope 12 includes a distal end 44 and a proximal end 45 and a longitudinal axis A extending therebetween.

Figure 2:
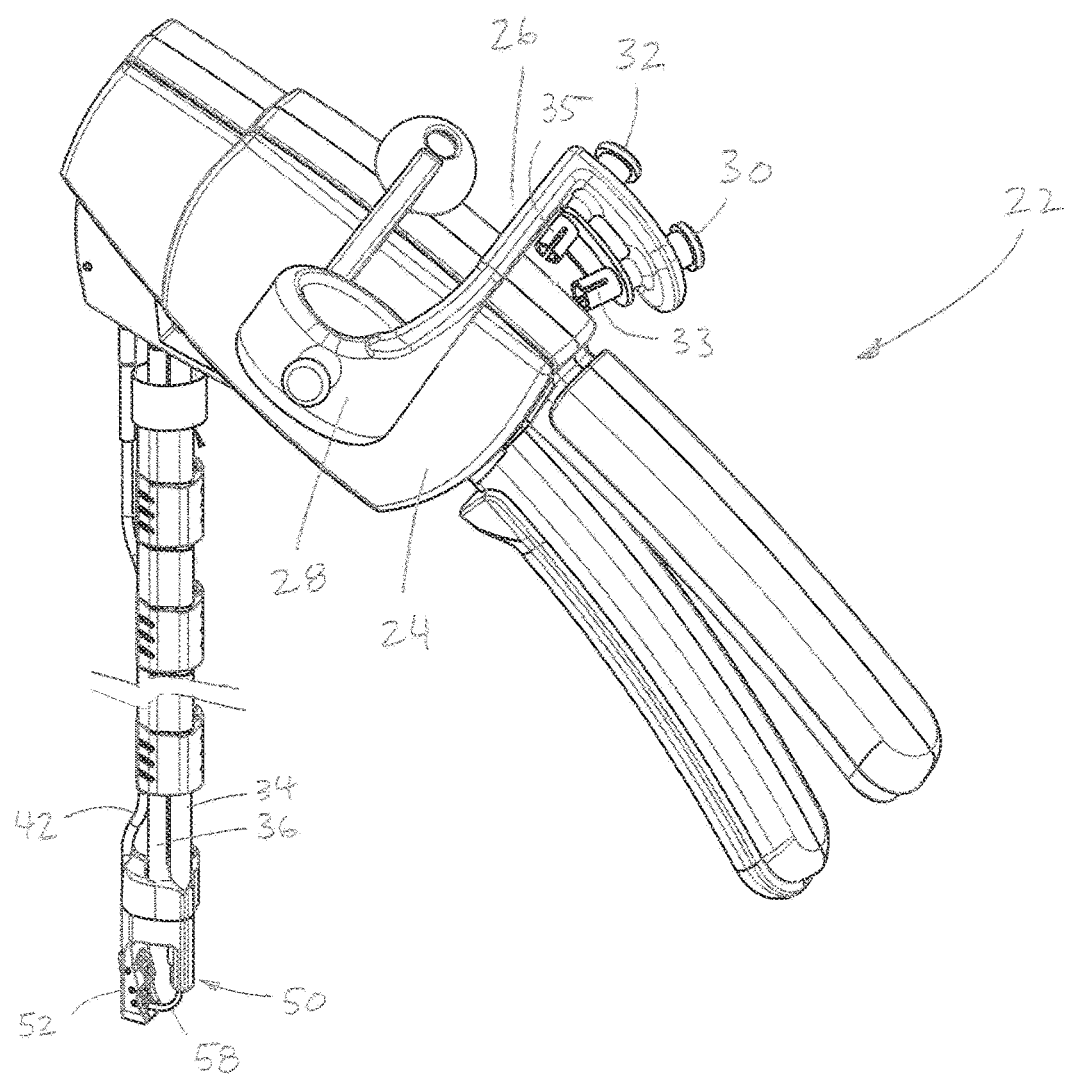
FIG. 2 is a proximal perspective view of a suturing device of the endoscopic suturing system of FIG. 1.

The suturing system 21 includes a suturing device 22 (FIG. 2), a needle assembly 70 (FIG. 4) movable through tissue by the suturing device 22, and first and second devices 38, 40 used in association with the suturing device 22 (FIGS. 2 and 4).

Figure 3:
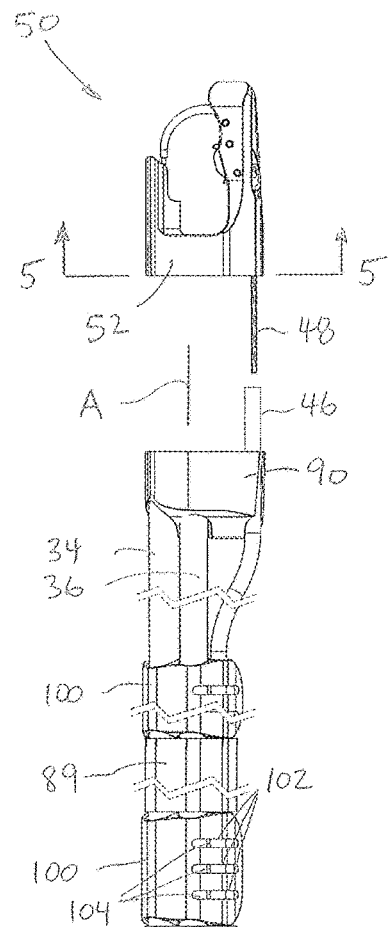
FIG. 3 is a broken side elevation view of a suturing device of the endoscopic suturing system of FIG. 1.

Referring to FIGS. 2 and 3, the suturing device 22 has a proximal operable handle 24 provided with a mounting bracket 26 and a collar 28 at which the handle is removably coupled to endoscope 12. The bracket 26 includes first and second instrument ports 30, 32 at which instruments can be received into first and second lumen 34, 36, respectively. First and second tubular connectors 33, 35 are aligned with the ports 30, 32 that couple the ports 30, 32 to the first and second lumen 34, 36.

A transmission assembly 42 includes a transmission sheath 46 and a transmission cable 48 displaceable within the transmission sheath 46, both coupled relative to the handle 24. The transmission sheath 46 is coupled relative to a first portion of the handle (i.e., a stationary member), and the transmission cable 48 is coupled to a second portion of the handle (i.e., a movable lever), such that when the handle 24 is operated the cable 48 is displaced within the transmission sheath 46.

The first and second lumens 34, 36 and the transmission assembly 42 extend from the proximal handle 24, along the outside of the endoscope 12, to a distal cap assembly 50. The distal cap assembly 50 is adapted to be mounted at the distal end 44 of the endoscope 12, and the handle 24 remotely operates the cap assembly 50 via the transmission assembly 42.

Referring to FIG. 4, the cap assembly 50 includes a mount 54, U-shaped support bracket 54 extending distally from the mount, and a needle arm 58 rotatably mounted on the bracket 52 with a first pin 60. A bell crank 64 is rotatably mounted at a second pin 66 on the support bracket 54 and engages the needle arm 58 at intermeshing gears (not shown). The distal end of the transmission cable 48 of the transmission assembly 42 is attached to the bell crank 64 at a clevis 68. When the transmission assembly 42 is operated by the handle 24, it results in rotation of the bell crank 64 and consequent rotation of the needle arm 58 between the open and closed positions.

The needle assembly 70 is coupled to a needle mount 83 at an end of the needle arm 58. The needle assembly 70 includes a tubular needle body 74, a needle tip 76, and suture 78 coupled to the needle body. The needle body 74 includes a side opening 80 through which the suture 78 extends, a first end 82 at which the needle assembly is coupled to the needle mount 83, and a second end 84 to which the tip 76 is coupled. The tip 76 defines a tissue-piercing taper. The suture 78 may be formed of any materials commonly available for surgical suture such as nylon, polyolefins, PLA, PGA, stainless steel, nitinol and others. One suitable needle assembly is described in more detail in previously incorporated U.S. Pat. No. 9,198,562.

Figure 5:
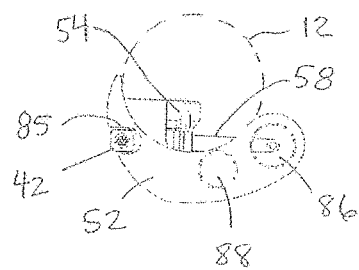
FIG. 5 is a cross-section view through line 5-5 in FIG. 3.

Turning to FIG. 5, the mount 52 of the cap assembly 50 also includes a side recess 85 into which the transmission assembly 42 is received, and a first throughbore 86 and a second throughbore 88. The first throughbore 86 is positioned in alignment with both the needle mount 83 of the needle arm 58 and needle assembly 70 when the needle arm 58 is in the closed position. A tissue guide 87 extends distally on the mount 52 from over the first throughbore 86 and provides a surface on which to stabilize tissue as it is pierced by the needle assembly 70. The second throughbore 88 is positioned between the first throughbore 86 and the support bracket 54. More particularly, the axial center of the second throughbore 88 is positioned between the first throughbore 86 and the pin 60 (or axis) on which the end effector rotates. The first and second throughbores 86, 88 may be parallel to each other and the longitudinal axis A of the endoscope, or the second throughbore 88 may be obliquely angled relative to the first throughbore 86 so as to direct the second device 40 at a particular orientation into the needle path, as described further below. The mount 52 is structured such that when the cap assembly 50 is coupled to the endoscope 12, as described below, the first and second throughbores 86, 88 are positioned radially outside the profile of the endoscope.

Figures 6, 7:
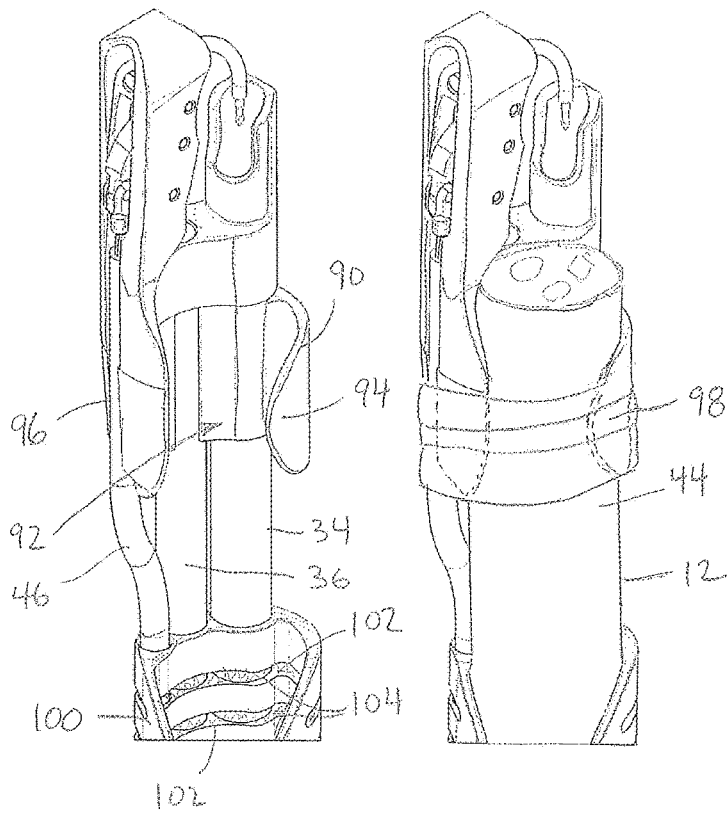
FIG. 6 is a perspective view of the distal end of the suturing device of FIG. 3.
FIG. 7 is a view similar to FIG. 6 shown in combination with an endoscope and with a banding material.

Referring to FIGS. 3 and 5, the distal end of the first lumen 34 is fixed in the first throughbore 86, and its proximal end is coupled to a first connector 33 on the handle bracket 26. The distal end of the second lumen 36 is fixed in the second throughbore 88, and its proximal end is coupled the second connector 35 on the handle bracket 26. The first and second lumen 34, 36 may be defined by discrete catheters (as shown in FIGS. 3 and 6) or may be defined as separate lumen of a common catheter. Further, the catheters 34, 36 (or common catheter) may be covered in a common sheath 89 along at least a portion of their lengths. The common sheath 89 may extend along the entire length of the catheters 34, 36, a partial length, or may be provided in sections along selected portions of the catheters 34, 36.

Turning to FIGS. 1, 3, 4 and 6, the first lumen 34 is adapted to receive a first device 38 that has a distal end effector that can receive and grasp the needle assembly 70. The second lumen 36 is adapted to receive a second device 40 that has a distal end effector that can engage tissue, and draw the tissue back into the path of the needle so that the tissue can be pierced by the needle assembly 70 as the needle assembly is moved from the open to the closed position.

The cap assembly 50 is secured to the distal end 44 of the endoscope 12 with a peripheral engagement structure that is adapted to be positioned about greater than 180° of the circumference of the distal end of the endoscope. In one embodiment, the structure is a cap clip 90 provided in abutting relationship to the mount, and preferably integrated with the mount 52. The clip 90 includes an opening 92, and an arm 94 that may be resiliently deformed to allow the distal end 44 of the endoscope 12 access through the opening 92 and then released to capture the distal end of the endoscope within the clip. The clip 90 may be formed from ABS plastic, other suitable plastics, elastic materials, as well as polymer-coated metals. The distal end of the clip 90 abuts against the proximal end of the mount 52. The first and second lumen 34, 36 extend within the clip 90, and a peripheral recess 96 is provided in the clip to receive the transmission assembly in a relatively flush configuration. A tape or cohesive banding 98 may be used over the clip 90 and distal end 44 of the endoscope to additionally secure the cap assembly relative to the endoscope during use. (FIG. 7) By way of example, a surgical-grade tape or silicone cohesive banding may be used.

Referring to FIGS. 3 and 6, a plurality of ancillary clips 100 are provided about the first and second lumen 34, 36 and transmission assembly 42 and forming a body that is adapted to extend greater than 180° about the circumference of the endoscope 12. The clips are adapted to secure the first and second lumen 34, 36 and transmission assembly 42 at various displaced locations to the endoscope 12. The ancillary clips 100 include transverse slots 102 that may be filled with a material or an adhesive 104, such as a polymer and optionally silicone. The filling material 104 has a higher coefficient of friction than the body of the clip to enhance the grip of the clip about the endoscope. The ancillary clips 100 are longitudinally spaced apart along the lumens 34, 36 and transmission assembly 42 to allow suitable flexure and operation of the first and second devices 38, 40 extending within the first and second lumen 34, 36, as well as flexure and operation of the transmission assembly 42. The spaced apart ancillary clips 100 may be interposed with portions of the common sheath 89.

In light of the above, the suturing device may be prepared for use in conjunction with an endoscope as follows. The cap assembly 50 is attached to the distal end 44 of the endoscope 12, with the cap clip 90 being opened to laterally receive the endoscope, and then released to secure the cap assembly 50 and endoscope 12 relative to each other. The first and second lumen 34, 36 and transmission assembly 42 are coupled along the endoscope 12 with the ancillary clips 100. The collar 28 is properly positioned at the proximal handle 45 of the endoscope 12. The first device, a needle capture instrument 38 loaded with a needle assembly 70, is advanced through the first port 32, into the first lumen 34 and to the cap assembly 50. Suitable needle capture devices 38 are described in detail in previously incorporated U.S. Pat. No. 8,679,136. The needle assembly 70 is loaded onto the needle arm 58, with the suture 78 extending parallel to the needle capture instrument 38 within the first lumen 34.

Figure 8:
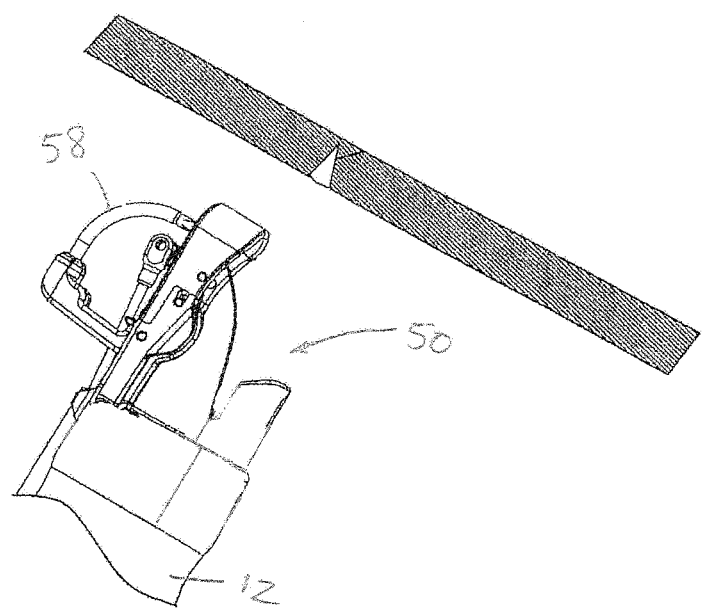
FIGS. 8-12 illustrate use of the endoscopic suturing system to endoscopically suture tissue.
Figure 9:
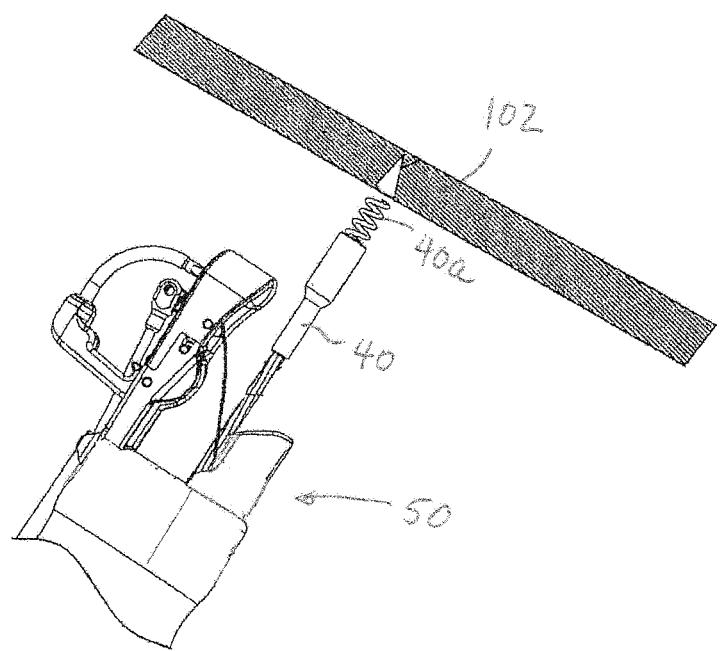
Figure 10:
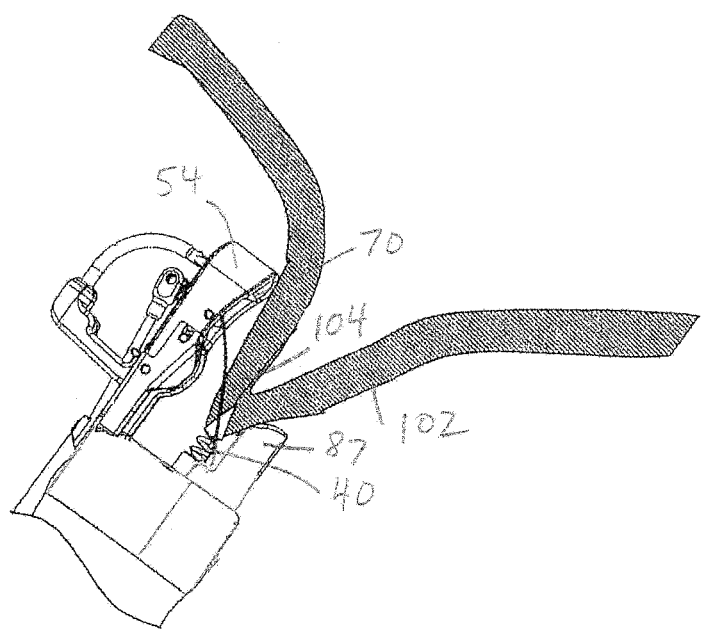
Figure 11:
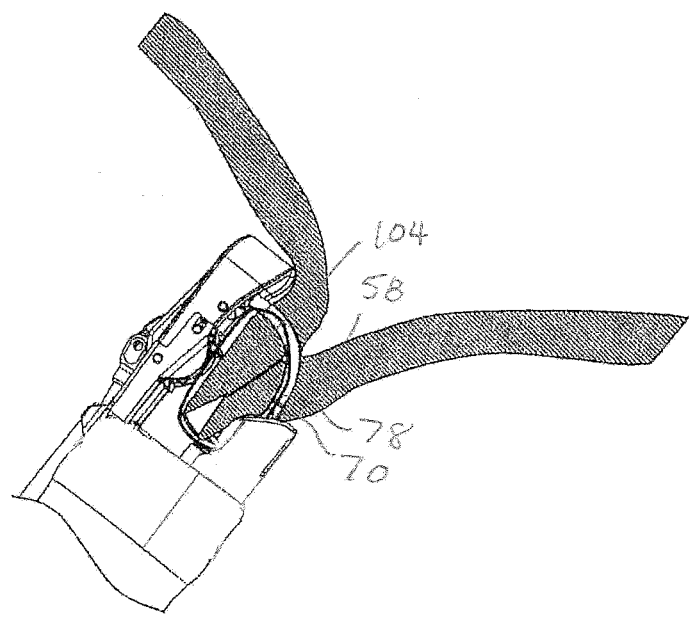
Figure 12:
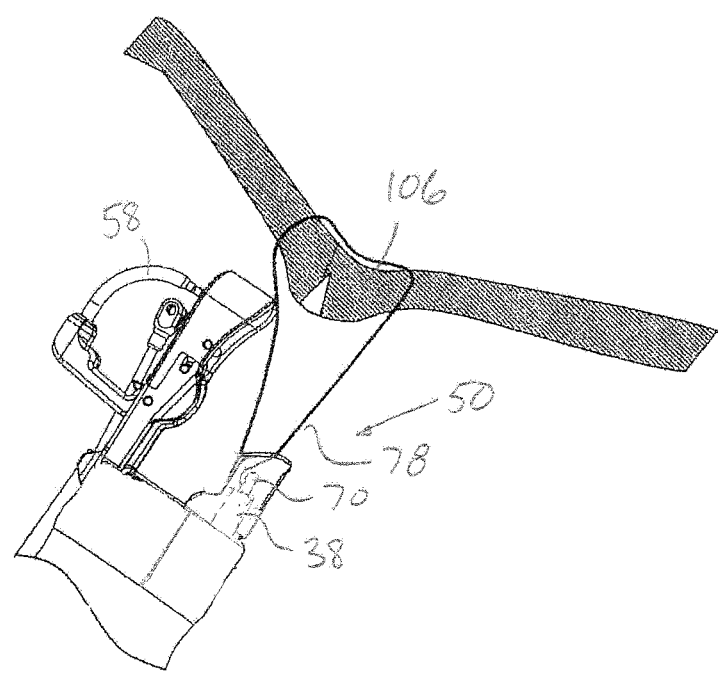

With reference to FIGS. 1 and 8, the distal end of the endoscope 12 and cap assembly 50 of the suturing device 22 are advanced into a natural orifice of a patient, optionally through a guide tube (not shown), and approached to target tissue 102. The handle 24 of the suturing device 22 is operated to move the needle arm 58 into the open position, as shown in FIG. 8. Turning to FIG. 9, the end effector of the second device, e.g., a tissue retractor 40 having a helical coil 40a at its distal end, is advanced through the second port 32, into the second lumen 36 (FIG. 3) and out the second throughbore 88 (FIG. 5), and beyond the cap assembly 50. Suitable tissue retractor instruments are described in detail in previously incorporated U.S. Ser. No. 13/539,661. Other tissue retractors, including forceps, may also be used. The helical coil 40a is operated to engage target tissue 102. The tissue retractor 40 is withdrawn to draw the tissue 102 against the tissue guard 87 and into a fold 104 located within the path of the needle assembly 70; i.e., between the bracket 54 and needle guide 87, as shown in FIG. 10. The orientation of the second throughbore 88, either parallel or obliquely angled relatively to the first throughbore 86, is adapted to guide the tissue retractor to engage and retract tissue into the needle path. The handle 24 is then operated to move the needle arm 58 into the closed position, thereby piercing the tissue fold 104 and passing the needle assembly 70 with suture 78 through the tissue fold during the movement. When the needle arm 58 is in the closed position, the needle is received within the distal end of the needle capture device 38 (FIG. 4). The needle capture device 38 is operated to securely engage the needle 70. The handle 26 is then operated to move the needle arm 58 toward the open position, thereby disengaging the needle arm 58 from the needle assembly 70, which remains in the needle capture device 38 (FIG. 12). The tissue retractor 40 is also released from the tissue and withdrawn back through the second lumen 36. The endoscope 12 is then moved to displace the cap assembly 50 relative to the sutured tissue 106. The needle 70 and suture 78 may be secured onto the tissue, such as by knotting or cinching, or the needle may be repositioned on the needle arm and additional suture loops may be formed within adjacent or other areas of tissue. Once the suturing is complete, the needle arm 58 is returned to a closed position, and the endoscope 12 and suturing device 22 are removed from the patient.

The suturing assembly is then released from over the endoscope by releasing the cap clip and ancillary clips from over the endoscope 12 and releasing the collar 28 from the proximal end of the endoscope.

Turning now to FIGS. 13 to 15, another embodiment of a suturing system 322 is shown that is substantially similar to suturing system 22 described above, but which includes variations on the peripheral engagement structure. In distinction from the cap clip 90 with resilient arm 94 of the earlier embodiment, the suturing system 322 includes at least one and preferably a plurality of straps 392 that are structured to retain the distal end 44 (FIG. 14) of the endoscope adjacent a cap mount 350. The straps 392 are preferably elastic and may be formed from polyurethane, silicone rubber, or similar material. The cap mount 350 defines at least one strap engaging slot 352 for the at least one strap 392. For each strap 392, one end 356 is adapted to be retained relative to the cap assembly 350 near the strap engaging slot 352, while another end 394 is configured to pass through the slot 352 to form a loop 396 sufficiently sized to receive the distal end of the endoscope.

The strap engaging slot 352 and the strap 392 are configured to provide resistance to pulling the strap 392 through the slot 352. Thus, when the end 394 of the strap 392 is pulled through the slot 352 and the strap 392 is released, the loop 396 formed by the strap 392 will be maintained without the strap 392 having to be further tightened. In one embodiment, the width of the slot 352 is made slightly smaller than the thickness of the corresponding strap portions 392 passing through the slot 352 so that the strap 392 in the slot 352 will be compressed and frictionally engaged by the slot 352.

End 356 of strap 392 has a wedge or teardrop profile, with a flared portion 356a terminating in a stop 356b. The flared portion 356a is configured to engage an opposing surface adjacent end 394 of the strap, to provide compression as the strap is drawn through the slot 352. The stop 356b, when fully seated within a mouth 393 of the slot 352, provides a locking engagement with the opposing surface adjacent end 394. Thus, when the strap 392 is pulled through the slot 352 and the stop 356b is fully seated, the strap 392 frictionally engages the flared portion 356a to compress the strap 392 with sufficient resistance to prevent loosening of the strap 392. Retention is further obtained by the tail end 352 of the strap 392 contorting around an edge of the endcap, with the wedge shape forcing the tail end to fold over the edge.

However, as discussed above, if the stop 356b of the strap 392 is not fully seated within the mount 350 of the cap assembly, the attachment and interface between the distal end 44 of the endoscope and the cap assembly 350 would not be as designed and intended. Then, it is possible that environmental forces and conditions could result in inadvertent release of straps 392 and loosening of the cap assembly 350 relative to the endoscope 44.

Figure 17:
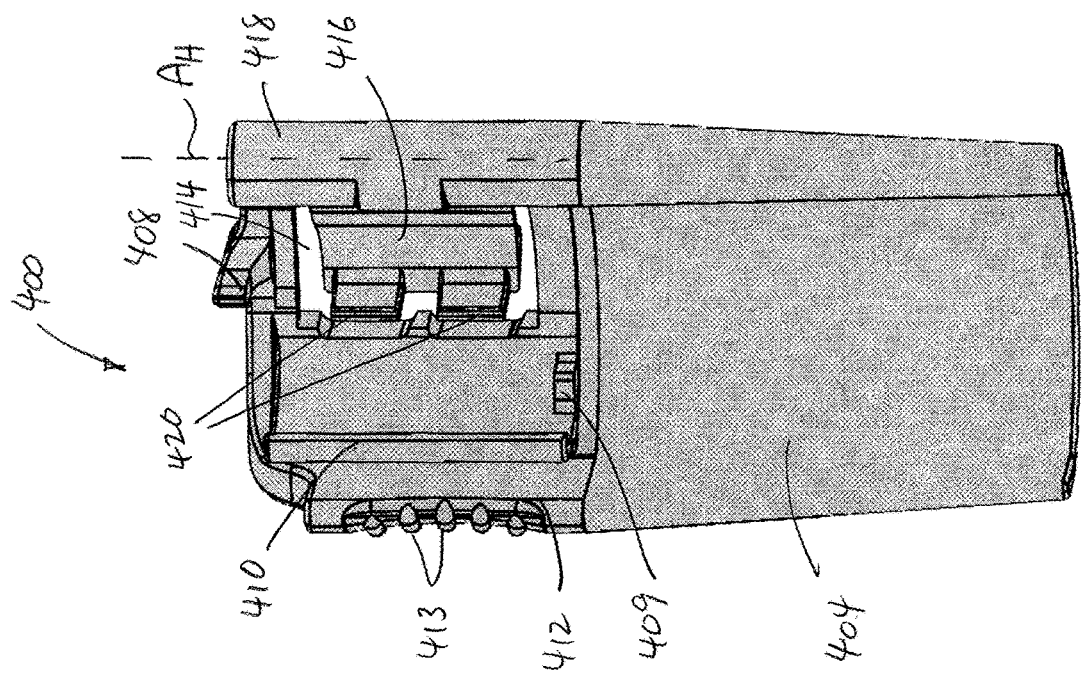
FIG. 17 is a second (interior) side elevation view of the tool of FIG. 16.
Figure 16:
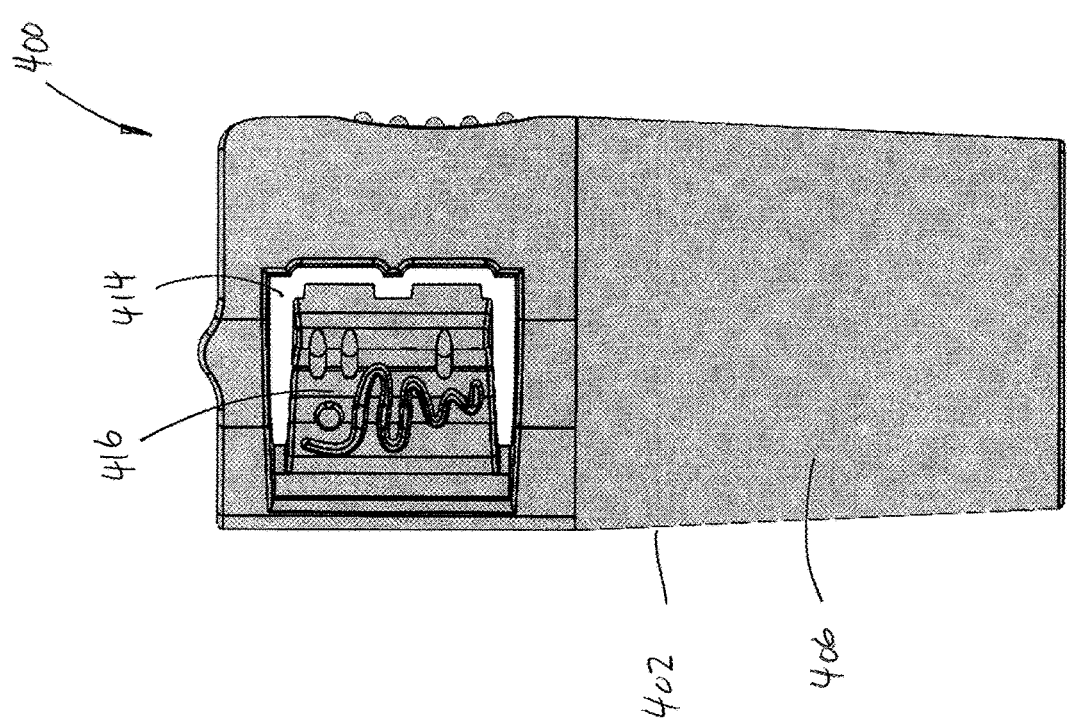
FIG. 16 is a first (exterior) side elevation view of a tool for assembly the cap assembly relative to an endoscope.
Figure 18:
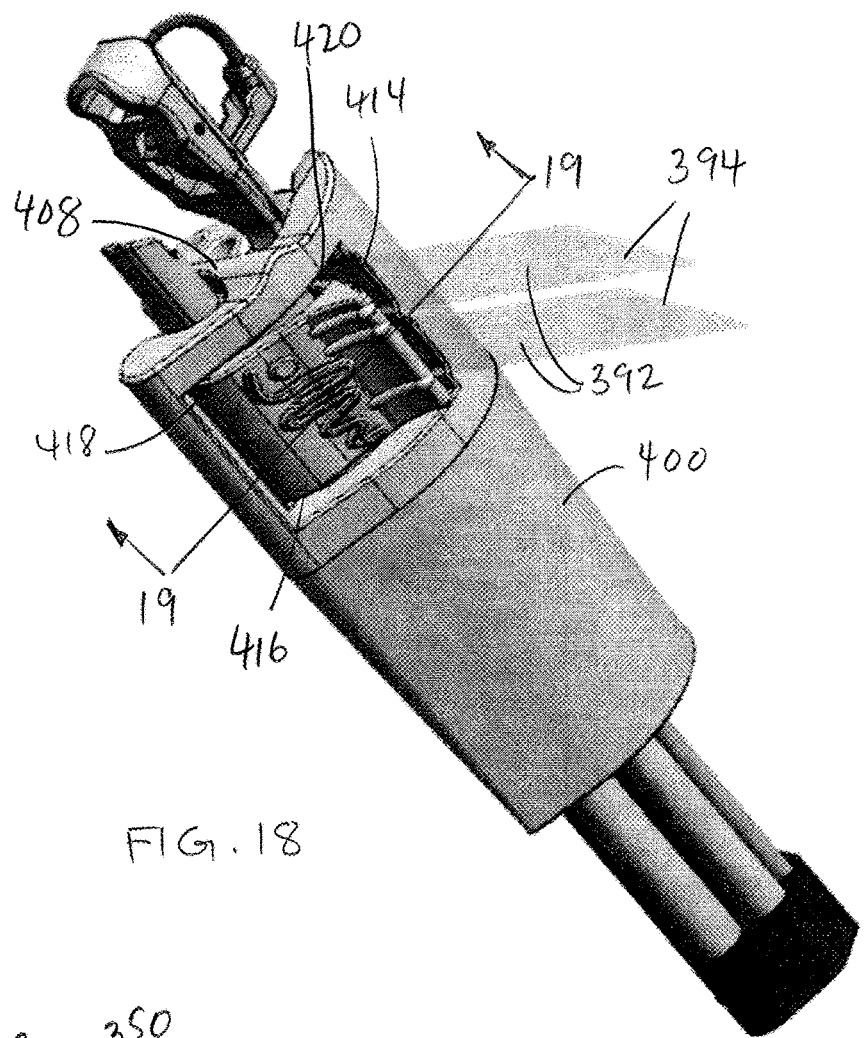
FIG. 18 is a perspective view of the cap assembly of FIG. 13, an endoscope, and the tool of FIG. 16.

In accord with an aspect of the invention and referring to FIGS. 16 and 17, a tool 400 has been designed to facilitate proper seating of the end 356 (FIG. 15) of the straps 392 in the mount 350, and thus fully securing the cap assembly 350 relative to the distal end of the endoscope. The tool 400 includes a body 402 adapted to partially surround the mount 350. The body 402 includes an inner surface 404 for contacting the mount, and an outer surface 406 forming a hand-hold. The body 402 includes a distal stop 408 and a proximal stop 409 for aligning the mount 350 therebetween, a retainer 410 that engages the mount 350 to retain the mount relative to the body, and a release portion 412 for releasing the retainer 410 from the mount 350. The release portion 412 includes a textured finger grip 413. A window 414 is defined in the body 402, and a swing arm (or tab) 416 is mounted on a hinge 418 and rotatable relative to the body 402, and particularly the window 414, about an axis AH. The hinge 418 may be a living hinge or include a pin. The swing arm 416 includes at least one pusher 420 at its free end adapted to move through the window 414 and toward the mount 350 as the swing arm 416 is rotated on axis AH. When the inner surface 404 and retainer 410 of the tool engage the mount 350, the swing arm 416 may be rotated on the body 402 to cause the pushers 420 to move through the window 414 and contact the end 356 of each strap 392 and force the stop 356b into a fully seated position, recessed within the strap slot 352.

Figure 19:
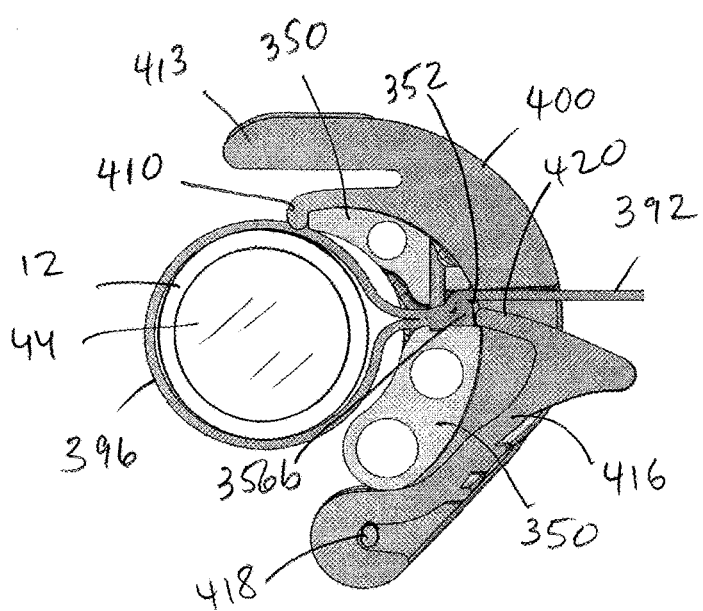
FIG. 19 is a section view across line 19-19 in FIG. 18.
Figure 26:
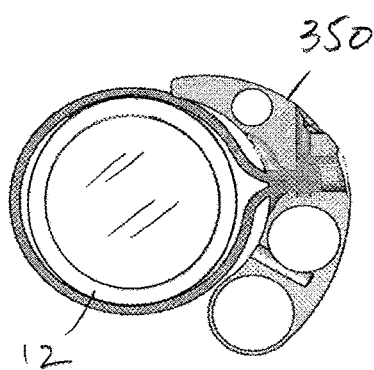
FIG. 26 is a view similar to FIG. 19 showing the cap assembly properly assembled relative to the endoscope.
Figure 20A:
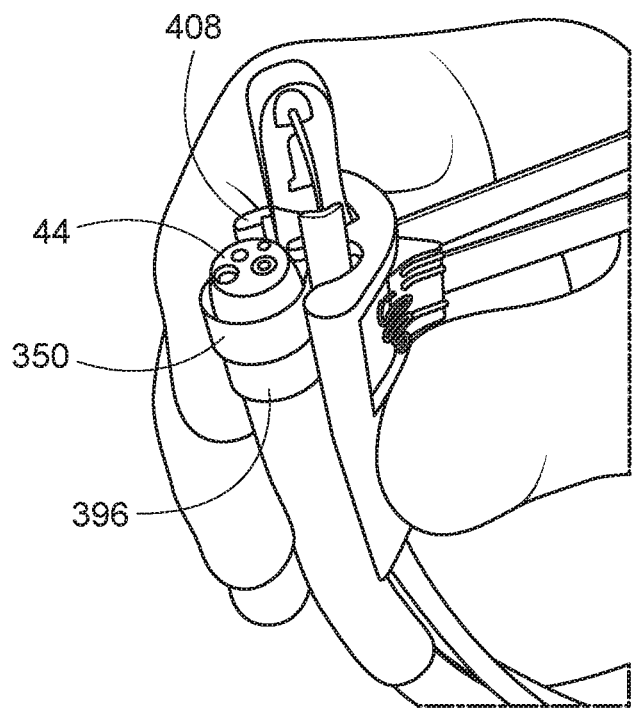
Figure 20B:
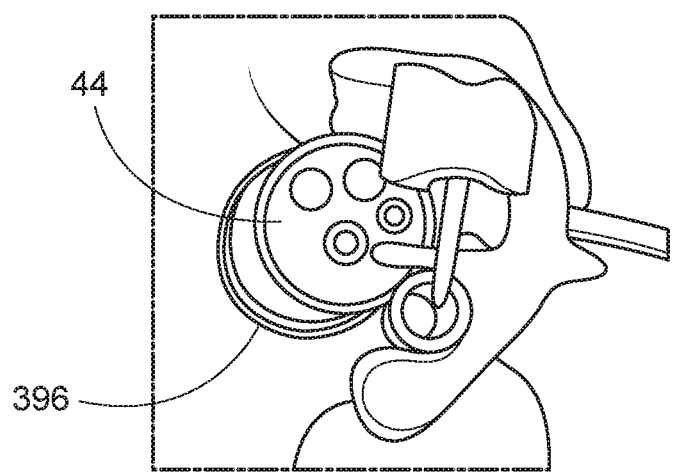
Figure 22:
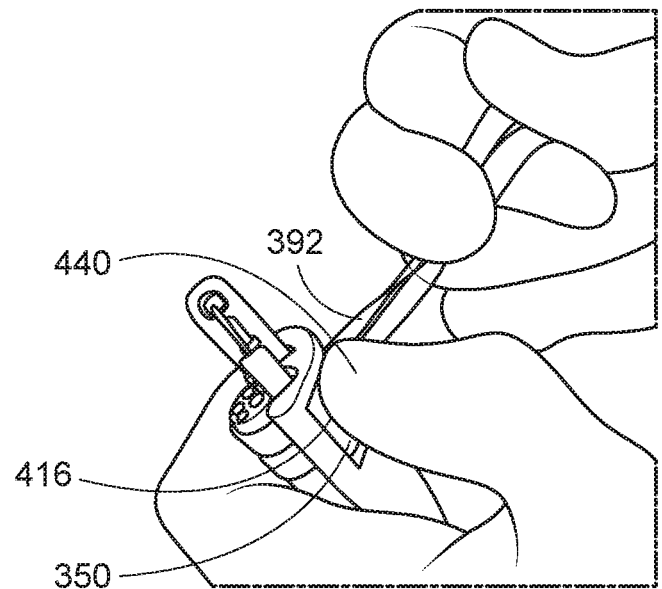
Figure 23:
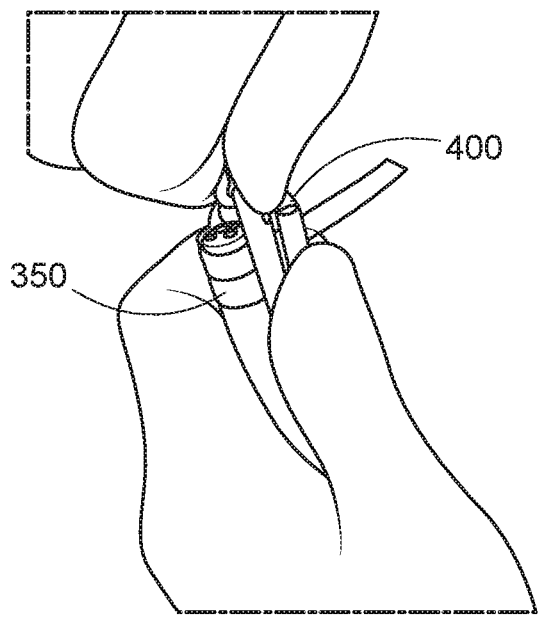
Figure 24:
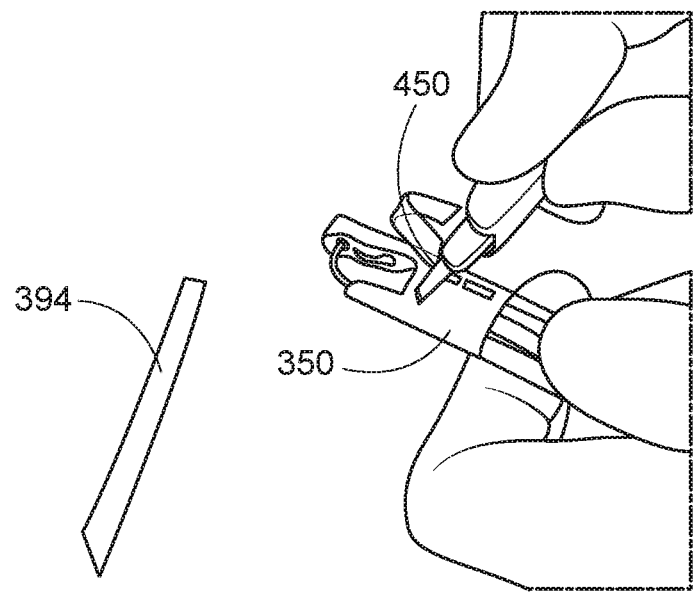
Figure 25:
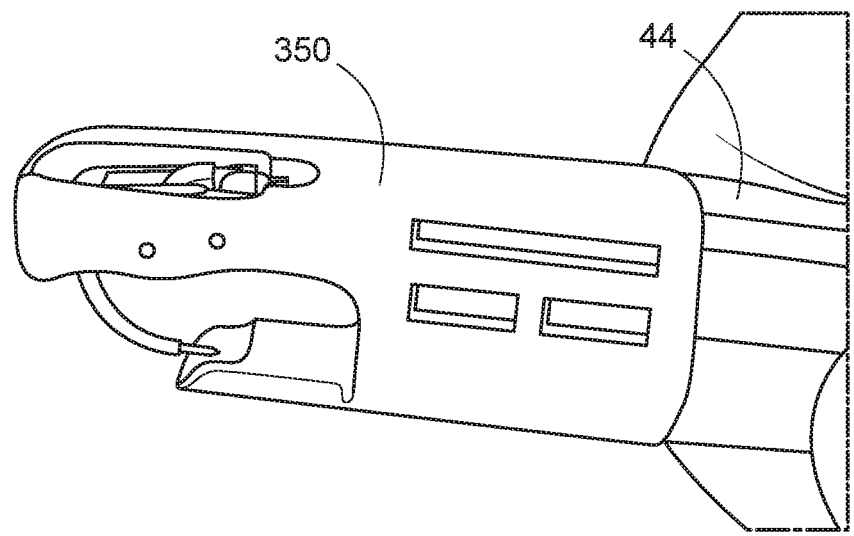

Turning to FIGS. 18 through 25, the use of the tool is now described. The mount 350 of the suturing instrument is preferably provided with the tool 400 pre-attached thereto. The straps 392 are preconfigured in the loop 396 (larger than the diameter of the distal end 44 of the endoscope) with the ends 394 of the straps 392 extending back through the window 414 opposite the hinge 418 (FIG. 19). To assemble the endoscope relative to the mount, the distal end 44 of the endoscope is positioned through the loop 396 defined by the straps and advanced until the distal stop 408 on the tool. (FIGS. 20A and 20B) Then, the free end 394 of each strap 392 is pulled to tighten the loops 396 about the end 44 of the endoscope. (FIGS. 21A and 21B) The swing arm 416 is then rotated about its hinge 418 and pressed with an operator's finger 440 to cause the pushers 420 to engage the stops 356b on the straps 392 and seat the stops in the respective slots 352 and flush with or below the circumference of the mount 350. (FIGS. 19 and 22) Then, the tool 400 is engaged at the grip 413 and manipulated to resiliently bend the release portion 412 to release the retainer 410 from about the mount 350. (FIGS. 19 and 23) A blade 450 is then used to trim the tail end 394 of the secured straps 392 substantially flush with the mount 350. (FIG. 24) The mount 350 is then fully and properly assembled relative to the distal end 44 of the endoscope and ready for use in a surgical procedure. (FIGS. 25 and 26)

There have been described and illustrated herein embodiments of a suturing system as well as a surgical treatment system and a tool for use therewith to mount the suturing system relative to an endoscope, as well as methods of using the aforementioned. While particular embodiments of the invention have been described, it is not intended that the invention be limited thereto, as it is intended that the invention be as broad in scope as the art will allow and that the specification be read likewise. Thus, while particular instruments and devices for advancement through the first and second lumen have been disclosed, it will be appreciated that other instruments can also be used through such lumen for like or even different purpose. Also, while the treatment system has been particularly described with respect to a cap assembly having an end effector in the form of a needle arm that carries a needle, it is recognized that alternatively one or more movable end effectors with other structure and purpose can be provided to the cap assembly. Also, while a tissue anchor in the form of a needle assembly has been described, the end effector can deploy different types of tissue anchors, including, e.g., clips. In addition, while a particular needle assembly has been described, other needle assemblies can similarly be used. Also, the size and instrument channel features of the endoscope with which the system is used is not critical, it is appreciated that various prior art systems cannot be properly used in a suturing operation in conjunction with endoscopes having fewer than two instrument channels, one for receiving a needle exchange device and the other for receiving a tissue retractor, whereas the present system is capable of complete operation without the provision of any channels through the endoscope. It will therefore be appreciated by those skilled in the art that yet other modifications could be made to the provided invention without deviating from its scope as claimed.

What is claimed is:

1. A distal cap assembly for use with an endoscope having a distal end, comprising:
 a) a distal cap apparatus having,
  i) a mount configured for mounting to the distal end of the endoscope, and
  ii) a strap connected to the mount and configured for banding about the distal end of the endoscope when the distal end of the endoscope is received in the mount,
  wherein the mount defines a strap slot configured to receive an end of the strap to configure the strap in the banded configuration; and
 b) a tool for mounting the distal cap relative to the endoscope, the tool having,
  i) a body adapted to partially surround the mount, the body having an inner surface facing the distal cap, an outer surface, a proximal end, and a distal end, and
  ii) an arm mounted to the body, the arm having a free end with a strap pusher, the arm adapted to be moved relative to the body to permit the strap pusher to push a portion of the strap into the strap slot to secure the strap in the strap slot.

2. The distal cap assembly according to claim 1, wherein the tool further includes a retainer that releasably couples the body relative to the mount.

3. The distal cap assembly according to claim 2, wherein the retainer is resilient.

4. The distal cap assembly according to claim 1, wherein the tool further includes a stop provided adjacent the distal end of the body of the tool to align the endoscope relative to the distal cap.

5. The distal cap assembly according to claim 1, wherein the body includes a window relative to which the arm is movable.

6. The distal cap assembly according to claim 1, wherein the strap pusher can extend radially inward of the inner surface of the body.

7. The distal cap assembly according to claim 1, wherein the strap is one of a plurality of straps of the distal cap apparatus, and the strap slot is one of a plurality of strap slots defined by the mount, the plurality of strap slots corresponding to the plurality of straps.

8. The distal cap assembly according to claim 1, wherein the strap slot is dimensioned to compress the strap when the strap is in the strap slot.

9. The distal cap assembly according to claim 1, wherein the strap is elastic.

10. The distal cap assembly according to claim 1, wherein the strap is in frictional engagement with the strap slot so that the frictional engagement retains the strap positioned relative to the strap slot.

11. A tool for use in mounting a distal cap apparatus relative to an endoscope, the distal cap apparatus having a mount configured for mounting to a distal end of the endoscope, a strap connected to the mount and configured for banding about the distal end of the endoscope when the distal end of the endoscope is received in the mount, and the mount defining a strap slot configured to receive an end of the strap to configure the strap in the banded configuration, the tool comprising:
 a) a body adapted to partially surround the mount, the body having an inner surface facing the distal cap, an outer surface, a proximal end, and a distal end; and
 b) an arm mounted to the body, the arm having a free end with a strap pusher, the arm adapted to be moved relative to the body to permit the strap pusher to push a portion of the strap into the strap slot to secure the strap in the strap slot.

12. The tool according to claim 11, wherein the tool further includes a retainer that is adapted to releasably couple the body relative to the mount.

13. The tool according to claim 12, wherein the retainer is resilient.

14. The tool according to claim 13, wherein the tool further includes a stop provided adjacent the distal end of the body adapted to align the distal end of the endoscope relative to the distal cap.

15. The tool according to claim 12, wherein the strap pusher can extend radially inward of the inner surface of the body.

16. The tool according to claim 11, wherein the body includes a window relative to which the arm is movable.

17. The tool according to claim 11, wherein the arm is movable on a hinge pin relative to the window.

18. A method for mounting an endoscope accessory relative to an endoscope having a distal end, comprising:
 a) providing the endoscope;
 b) providing the endoscope accessory, the endoscope accessory including,
  i) a mount configured for mounting to the distal end of the endoscope, and
  ii) a strap connected to the mount and configured for banding about the distal end of the endoscope when the distal end of the endoscope is received in the mount,
  wherein the mount defines a strap slot that receives an end of the strap to configure the strap in the banded configuration; and
 c) providing a tool to the endoscope accessory for securing the strap within the strap slot;
 d) drawing the strap through the strap slot and into tension about the distal end of the endoscope; and
 e) contacting a portion of the tool against a portion of the strap to secure the strap within the strap slot.

19. The method according to claim 18, further comprising:
 before drawing, aligning the distal end of the endoscope relative to a distal stop provided to the tool.

20. The method according to claim 18, further comprising:
 the drawing further includes drawing the strap through an opening in the tool.

21. The method according to claim 18, wherein the strap includes first and second ends, and both the first and second ends are received in or through the strap slot.

22. The method according to claim 21, further comprising:
 after the contacting, separating the tool from the distal cap apparatus.

23. The method according to claim 22, further comprising:
after the separating, cutting at least the first end of the strap flush with an outer surface of the mount.

24. The method according to claim 18, wherein the endoscope accessory includes a suturing device.

25. The method according to claim 18, wherein the endoscope accessory includes accessory instrument channels.

26. A method for mounting an endoscope accessory relative to an endoscope having a distal end, comprising:
   a) providing the endoscope;
   b) providing the endoscope accessory, the endoscope accessory including,
      i) a mount configured for mounting to the distal end of the endoscope,
      ii) a strap connected to the mount and configured for banding about the distal end of the endoscope when the distal end of the endoscope is received in the mount,
      wherein the mount defines a strap slot that receives an end of the strap to retain the strap in the banded configuration, and
      iii) a structure provided to the mount adapted to secure the strap within the strap slots;
   c) drawing the strap through the strap slot and into tension about the distal end of the endoscope; and
   d) contacting a portion of the structure against a portion of the strap to secure the strap within the strap slot.

27. The method of claim 26, wherein the portion of the structure is moved from a radially exterior location relative to the slot to be flush with or within the slot.

* * * * *